(12) United States Patent
Griffin et al.

(10) Patent No.: US 9,532,874 B2
(45) Date of Patent: Jan. 3, 2017

(54) APPARATUS AND METHOD FOR HEART VALVE REPAIR

(75) Inventors: Mark Griffin, Louisville, KY (US); Benjamin E. Morris, Jeffersonville, IN (US); Eric E. Bielefeld, Floyds Knobs, IN (US); Gregory R. Furnish, Louisville, KY (US); Wayne Allen Johnson, Jeffersonville, IN (US)

(73) Assignee: St. Jude Medical, Inc, St. Paul, MN (US)

( * ) Notice: Subject to any disclaimer, the term of this patent is extended or adjusted under 35 U.S.C. 154(b) by 287 days.

(21) Appl. No.: 14/127,575

(22) PCT Filed: Jun. 12, 2012

(86) PCT No.: PCT/US2012/042063
§ 371 (c)(1),
(2), (4) Date: Dec. 19, 2013

(87) PCT Pub. No.: WO2012/177441
PCT Pub. Date: Dec. 27, 2012

(65) Prior Publication Data
US 2014/0128970 A1    May 8, 2014

Related U.S. Application Data

(60) Provisional application No. 61/499,295, filed on Jun. 21, 2011.

(51) Int. Cl.
*A61F 2/24*         (2006.01)
*A61B 17/064*       (2006.01)
(Continued)

(52) U.S. Cl.
CPC ........... *A61F 2/2487* (2013.01); *A61B 17/064* (2013.01); *A61B 17/068* (2013.01);
(Continued)

(58) Field of Classification Search
CPC ....... A61B 17/08; A61B 17/10; A61B 10/164; A61B 10/168; A61B 2017/0647; A61B 2017/2926; A61B 2017/00429; A61B 17/068; A61B 17/0487; A61B 17/22; A61B 17/122; A61B 17/0643; A61B 2017/00243; A61B 2/2487; A61B 17/282; A61B 2017/2825; A61B 17/2833; A61B 2017/2906; B23K 37/0426; B25B 7/02; B25B 7/22; Y10T 29/539
(Continued)

(56) References Cited

U.S. PATENT DOCUMENTS

| | | | |
|---|---|---|---|
| 6,743,239 B1 * | 6/2004 | Kuehn | A61B 17/0643 464/149 |
| 2003/0065358 A1 * | 4/2003 | Frecker | A61B 17/29 606/205 |

(Continued)

OTHER PUBLICATIONS

International Search Report for Application No. PCT/US2012/042063 dated Sep. 24, 2012.

*Primary Examiner* — David C Eastwood
*Assistant Examiner* — Mikail Mannan
(74) *Attorney, Agent, or Firm* — Lerner, David, Littenberg, Krumholz & Mentlik, LLP

(57) ABSTRACT

A device 10 for repairing mitral valve leaflets 2, 3 includes a jaw mechanism 15 that may be positioned adjacent a mitral valve leaflet 2, 3. The jaw mechanism 15 may move between an open position and a closed position by pivoting a first jaw relative 16 to a second jaw 18. The first jaw 16 may include a rivet 28 that may move from a stored position to an application position projecting away from the first jaw 16 when the jaw mechanism 15 is moved from the closed to the open position. Closing the jaws 16, 18 about a valve leaflet 2, 3 causes the rivet 28 to pierce the leaflet. The jaw (Continued)

mechanism 15 may then be rotated to wind the leaflet 2, 3 thereabout and again pierce the leaflet. The rivet 28 may then be released from the jaw mechanism 25 and the device 10 removed from the patient.

19 Claims, 8 Drawing Sheets

(51) Int. Cl.
  *A61B 17/068* (2006.01)
  *A61B 17/00* (2006.01)
  *A61B 17/29* (2006.01)

(52) U.S. Cl.
  CPC ............... *A61B 2017/00243* (2013.01); *A61B 2017/00429* (2013.01); *A61B 2017/0647* (2013.01); *A61B 2017/2926* (2013.01)

(58) Field of Classification Search
  USPC .................................................. 81/418, 419
  See application file for complete search history.

(56) References Cited

U.S. PATENT DOCUMENTS

| | | | |
|---|---|---|---|
| 2004/0059349 A1* | 3/2004 | Sixto, Jr. ............ | A61B 17/0643 606/139 |
| 2006/0004388 A1* | 1/2006 | Whayne ............. | A61B 17/0643 606/151 |
| 2007/0093857 A1 | 4/2007 | Rogers et al. | |
| 2010/0145361 A1* | 6/2010 | Francischelli ... | A61B 17/12009 606/139 |

\* cited by examiner

APPARATUS AND METHOD FOR HEART VALVE REPAIR

CROSS-REFERENCE TO RELATED APPLICATIONS

The present application is a national phase entry under 35 U.S.C. §371 of International Application No. PCT/US2012/042063, filed Jun. 12, 2012, published in English, which claims priority from U.S. Provisional Application No. 61/499,295, filed Jun. 21, 2011, entitled APPARATUS AND METHOD FOR HEART VALVE REPAIR, all of which are incorporated herein by reference.

BACKGROUND OF THE INVENTION

The present invention is related to heart valve repair, and more particularly to devices, systems, and methods for repair of a heart valve leaflet.

Properly functioning heart valves can maintain unidirectional blood flow in the circulatory system by opening and closing, depending on the difference in pressure from one side of the valve to the other. The two atrioventricular valves (mitral and tricuspid valves) are multicusped valves that prevent backflow from the ventricles into the atria during systole. They are anchored to the wall of the ventricle by chordae tendinae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendinae may stretch and thus become too long, or the chordae tendinae may be ruptured. As a result, the valve does not close normally. As a result of being stretched, the unsupported valve leaflet bulges back, or "prolapses," into the left atrium like a parachute. Thus, as the ventricle contracts, the abnormal leaflet may be propelled backwards, beyond its normal closure line and into the left atrium, thereby allowing blood to return to the left atrium and the lungs.

Mitral valve prolapse causes mitral regurgitation. Isolated posterior leaflet prolapse of the human heart mitral valve, i.e., prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, conventional methods of treating mitral valve prolapse include replacement of the mitral valve, clipping the two mitral valve leaflets to one another, and resection of the prolapsed segment using open heart surgery. Such surgical methods may be invasive to the patient and may require an extended recovery period.

There therefore is a need for further improvements to the current techniques for treating heart valve leaflet prolapse. Among other advantages, the present invention may address one or more of these needs.

BRIEF SUMMARY OF THE INVENTION

One aspect of the disclosure provides a device for repair of a heart valve leaflet. The device includes an elongated body having a proximal end and a distal end and a jaw mechanism on the distal end of the elongated body. The jaw mechanism includes a first jaw and a second jaw operable to pivot relative to one another between an open position and a closed position. In the open position, the jaw mechanism defines a receiving space between the first jaw and the second jaw. The device also includes a rivet mounted to the first jaw and movable from a stored position to an application position. In the application position, the rivet projects away from the first jaw toward the second jaw. The rivet also has a sharp free end adapted to pierce the heart valve leaflet. The movement of the jaw mechanism from the open position to the closed position with the heart valve leaflet in the receiving space and the rivet in the application position causes the rivet to pierce the heart valve leaflet.

In one example, the first jaw is fixed relative to the elongated body and the second jaw is pivotable relative to the first jaw. In another example, the device includes an operating mechanism for pivoting the second jaw into the open position. In another example, the device also includes a spring element interposed between the rivet and the first jaw for biasing the rivet towards the application position. In one alternative, the spring element includes at least one torsion spring. In another alternative, the first jaw has a compartment for receiving the rivet in the stored position, and the second jaw is configured to hold the rivet in the compartment when the secured jaw is in the closed position. In another example, the second jaw has a slot sized to receive the sharp free end of the rivet there through when the rivet is in the application position and the second jaw is in the closed position. In another example, the device also includes at least one sharpened structure projecting laterally from the second jaw for providing traction for the jaw mechanism as the jaw mechanism is rotated against the tissue of the heart valve leaflet. In another example, the first jaw has a tissue grasping surface and the second jaw has a tissue grasping surface. In this example, the tissue grasping surfaces of the first and second jaws confront one another in the closed position, and at least one of the tissue grasping surfaces being textured. In another example, at least a portion of the jaw mechanism is formed from an echogenic material. In another example, the second jaw has a thickness between a first surface facing toward the first jaw and a second surface opposite the first surface, and the rivet has a length greater than the thickness of the second jaw so that the rivet protrudes beyond the second surface of the second jaw when the second jaw is in the closed position.

Another aspect of the disclosure provides a method of repairing a heart valve leaflet in a patient. The method includes positioning a jaw mechanism adjacent the heart valve leaflet. The jaw mechanism includes a first jaw, a second jaw, and a rivet mounted to the first jaw in a stored position. The rivet has a sharp free end. The method also includes moving the jaw mechanism to an open position to create a receiving space between the first jaw and the second jaw, moving the rivet from the stored position to an application position in which the sharp free end of the rivet projects away from the first jaw toward the second jaw, capturing the heart valve leaflet in the receiving space, moving the jaw mechanism to a closed position in which the second jaw confronts the first jaw such that the sharp free end of the rivet pierces the heart valve leaflet at a first location and the heart valve leaflet is clamped between the first jaw and the second jaw, rotating the jaw mechanism so that the heart valve leaflet winds around the jaw mechanism, piercing the sharpened tip of the rivet through the heart valve leaflet at a second location different from the first location, and releasing the rivet from the first jaw.

In one example, the step of moving the jaw mechanism to the open position includes pivoting the second jaw member away from the first jaw member. In another example, the step of moving the rivet to the application position occurs as the jaw mechanism is moved to the open position. In another example, the rivet is biased from the stored position to the application position. In another example, maintaining the jaw mechanism in the closed position maintains the rivet in the stored position.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

DETAILED DESCRIPTION

As used herein, the terms "proximal" and "distal" are to be taken as relative to a user (e.g., a surgeon or an interventional cardiologist) using the disclosed devices. "Proximal" is to be understood as relatively close to the user and "distal" is to be understood as relatively farther away from the user. The invention will be described in connection with the repair of a mitral valve leaflet, but it may also be useful in the repair of other types of cardiac valves or in the gathering and riveting of other types of loose body tissue.

Figure 1:
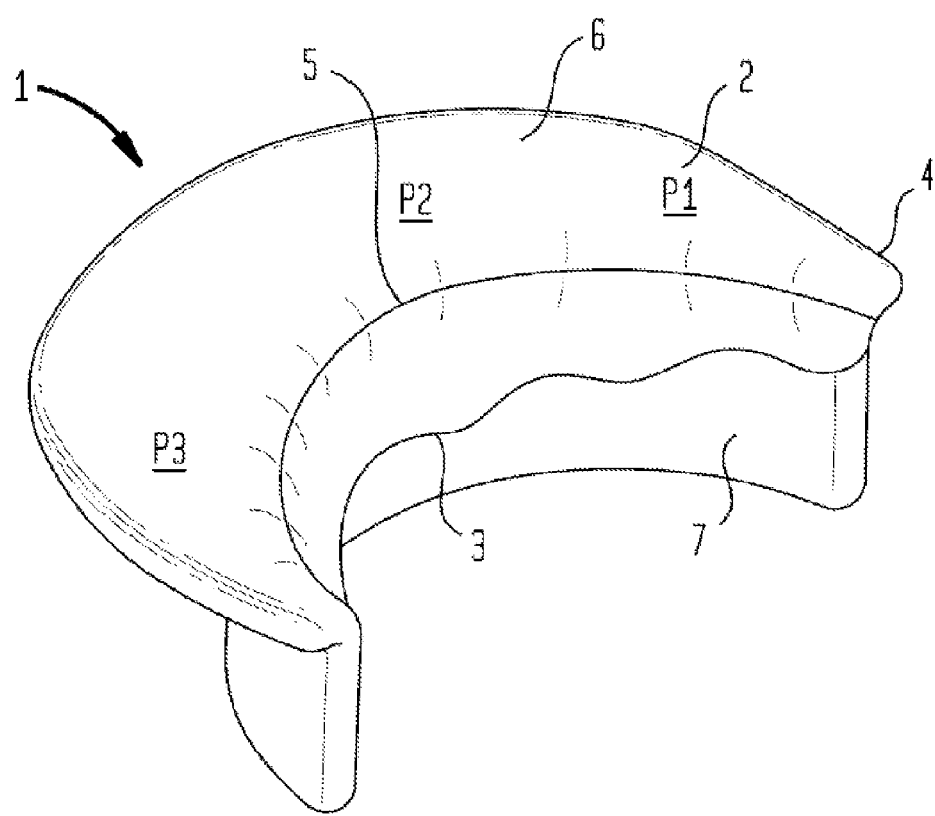
FIG. 1 is a diagrammatic perspective view of the posterior leaflet of a mitral valve.

As shown in FIG. 1, an exemplary mitral valve 1 includes a posterior leaflet 2 and an anterior leaflet 3. The leaflets 2 and 3 extend from an annulus 4 to a coaption line 5 where the leaflets meet. The posterior leaflet 2 has an upper portion 6 that is generally perpendicular to the direction of blood flow through the valve 1 and extends between the annulus and the coaption line 5. Additionally, the posterior leaflet 2 has a lower portion 7 that is generally parallel to the direction of blood flow through the valve 1 and extends below the coaption line 5. The posterior leaflet 2 has three scalloped portions P1, P2, and P3, any of which may include a portion that is billowed, loose, or floppy, and therefore be the cause of a prolapse condition of the valve. The inventive devices, systems, and methods described herein may be adapted to repair such a billowed, loose, or floppy portion of the posterior leaflet 2 or the anterior leaflet 3.

Figure 2:
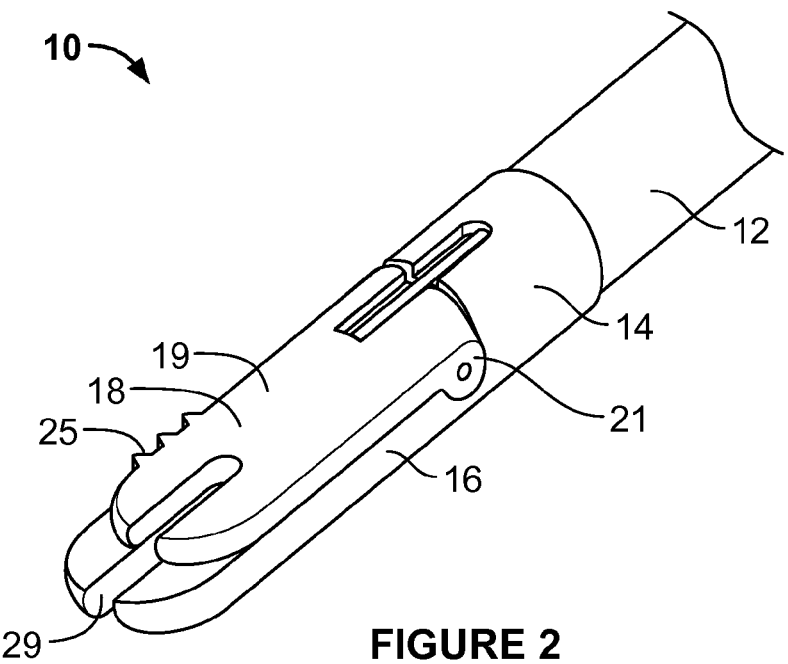
FIG. 2 is a perspective view of a distal portion of a device for repairing mitral valve leaflets in accordance with the present invention.

Referring to FIG. 2, an exemplary device 10 for repair of heart valve leaflet tissue may include an elongated body or catheter assembly 12 adapted to be inserted through the left atrium of a human heart so that a distal portion 14 of the catheter assembly may reach the patient's mitral valve for repair thereof.

Figure 3:
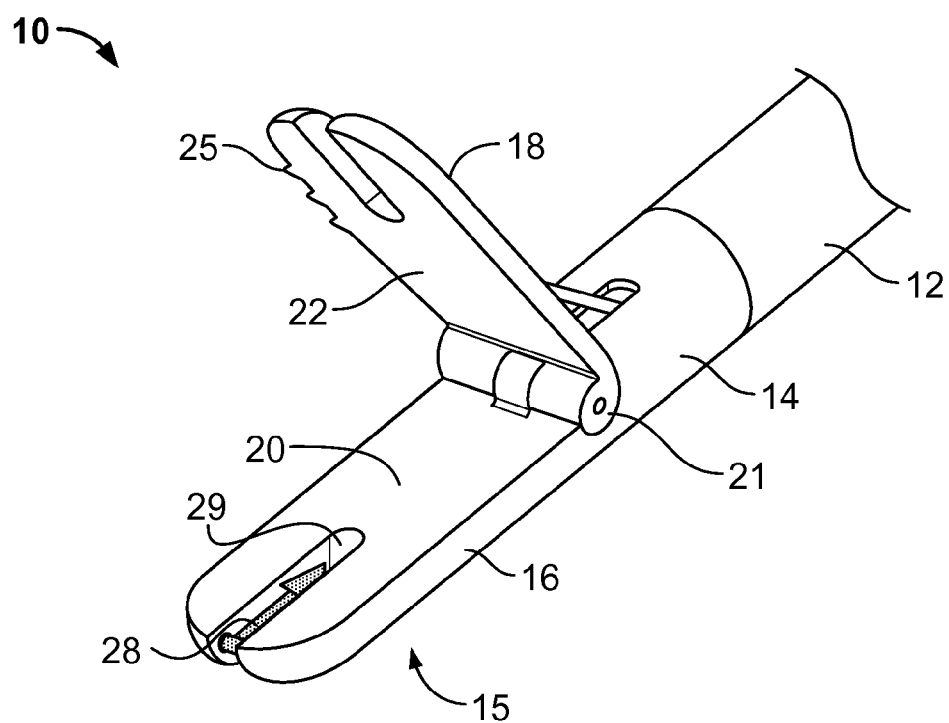
FIG. 3 is a perspective view of the device of FIG. 2 in an open position.

The distal portion 14 of the catheter assembly 12 may include a jaw mechanism 15 having a first jaw 16 and a second jaw 18. Although it is contemplated that both the first jaw 16 and the second jaw 18 may pivot, in a preferred arrangement, only one of the jaws will pivot while the other jaw remains fixed relative to catheter assembly 12. Having one of the jaws fixed will simplify the structure and operation of device 10, and will facilitate the accurate positioning of the jaw mechanism relative to the valve leaflet. Accordingly, in the description which follows, jaw 16 will be described as fixed relative to catheter assembly 12, while jaw 18 will be described as being capable of pivoting about pivot pin 21 relative to jaw 16 between open and closed positions. FIG. 2 depicts jaw 28 in the closed position, while FIG. 3 depicts jaw 18 in an open position.

Jaw 18 may have an outer surface 19 and an inner gripping surface 20, with the maximum distance between surfaces 19 and 20 defining the thickness of jaw 18. Similarly, jaw 16 may have an outer surface 17 (shown in FIG. 5) and an inner gripping surface 22, with the maximum distance between surfaces 17 and 22 defining the thickness of jaw 16.

In the open position, the space between the inner gripping surface 22 of jaw 16 and the inner gripping surface of jaw 18 may define a receiving space for receiving tissue. Preferably, gripping surfaces 20 and 22 are configured to complement one another when the jaw mechanism 15 is in the closed position. For example, both surfaces may be flat or may include a complementary curving. One or both of gripping surfaces 20 and 22 may also be knurled, grooved or otherwise textured to promote gripping of tissue. Jaw mechanism 15 preferably includes one or more prongs, teeth, or other somewhat sharpened structures 25 projecting laterally from one or both of jaws 16 and 18, the purpose of which will be described below.

Figure 4:
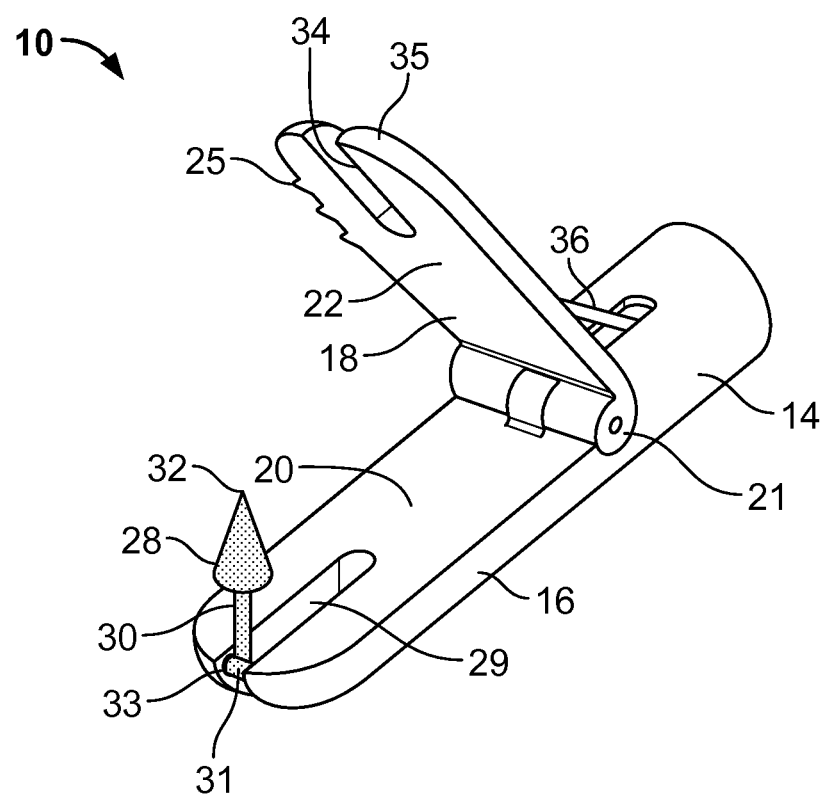
FIG. 4 is another perspective view of the device of FIG. 2 in an open position.

Jaw 16 may be configured to releasably hold a barb or rivet 28 for delivery to the target site and implantation into the leaflet tissue. In that regard, the inner surface 22 of jaw 16 may include a recessed compartment 29 which receives the rivet 28 in a stored position (shown in FIG. 3) as delivery device 10 is advanced to the target site. Rivet 28 may have an elongated body 30 with a rod-like shaft 31 at one end oriented substantially perpendicular to body 30, and a barbed tip 32 at the opposite or free end. Shaft 31 may be journaled in a pair of opposed slots or other recesses 33 on either side of compartment 29 for pivotally connecting rivet 28 to jaw 16. A torsion spring (not shown) may be assembled between shaft 31 and the recesses 33 on one or both sides of compartment 29 to bias rivet 28 from the stored position to an application position (shown in FIG. 4) in which the rivet protects out from compartment 29 at an orientation that is substantially perpendicular to the inner gripping surface 22 of jaw 16. Thus, when jaw mechanism 15 is in the closed position, the proximity of jaw 18 to the inner gripping surface 22 of jaw 16 will maintain rivet 28 in the stored position within compartment 29. However, when jaw 18 is pivoted away from jaw 16 to the open position, the biasing force exerted by the torsion springs will cause rivet 28 to move from the stored position to the application position. A tab or other structure on rivet 28 may cooperate with a corresponding structure on jaw 16 to limit the rotation of the rivet relative to jaw 16 so as to achieve the application position. It will be appreciated, of course, that rather than a torsion spring, other devices, such as a leaf spring or other spring structures, may be used to bias rivet 28 from the stored position to the application position. Moreover, rather than having rivet 28 biased to the application position, device 10 may include a mechanical structure for manually moving the rivet from the stored position to the application position as desired. Once in the application position, a detent, ratchet or other structure may lock rivet 28 in place, so that any torque exerted on the rivet does not cause it to readily pivot towards the stored position.

So that rivet 28 does not interfere with the movement of jaw 18 from the open position to the closed position when the rivet is in the application position, jaw 18 may be provided with a slot 34 which extends partially along the length of the jaw from its distal end 35. Slot 34 has a width sufficient to receive the barbed tip 32 of the rivet when the rivet is in the application position. However, with jaw mechanism 15 in the closed position and rivet 28 in the stored position, the closed end of slot 34 overlies the rivet to prevent the rivet from pivoting out from compartment 29 in jaw 16. As an alternative to slot 34, jaw 18 may be formed with a length that is less than the length of jaw 16, i.e., the distal ends of the jaws are not coterminus. In such an arrangement, jaw 18 would have a length between pivot pin 21 and its distal end 35 sufficient to at least partially cover rivet 28 when the rivet is in the stored position and jaw mechanism 15 is in the closed position, thereby enabling jaw 18 to maintain the rivet in the stored position. However, the length of jaw 18 would be such that the distal end 35 thereof would lie proximally of the recesses 33 in which rivet 28 is journaled when jaw mechanism 15 is in the closed position, and thus would not interfere with the rivet when the rivet is in the application position.

All or part of the distal portion 14 of device 10, such as jaw 16, jaw 18, and/or rivet 28, may be made of one or more echogenic materials to enable these structures to be more easily visualized using three-dimensional echocardiography while the device is in use in a patient.

The device 10 may further include an operating mechanism for pivoting jaw 18 between the open and closed positions. In one example, shown in FIG. 3, a linkage 36 may be pivotably connected at one end to jaw 18 at a position distal to pivot pin 21. At its other end, linkage 36 may be pivotably connected to an elongated control rod (not shown). The control rod may extend to a handle (not shown) at the proximal end of catheter assembly 12. By depressing, sliding, or rotating an actuating member, such as a button or slide on the handle, the control rod may be moved proximally relative to the catheter assembly 12. Through linkage 36, the proximal movement of the control rod will cause jaw 18 to rotate on pivot pin 21 into the open position shown in FIG. 3. Subsequently depressing, sliding, or rotating the actuating member on the handle may move the control rod distally relative to the catheter assembly 12, and through linkage 36, will cause jaw 18 to rotate on pivot paint 21 into the closed position shown in FIG. 2.

To use the device 10 for transcatheter repair of heart valve leaflet tissue, a rivet 28 is first loaded into the recess 29 in jaw 16. This may be done by the manufacturer during the assembly of device 10, or may be done by the user or an assistant prior to the use of the device. The rivet 28 may be loaded during the manufacturing process. In some examples, the device may hold multiple rivets in succession, loaded during the manufacturing process or by the user at the time of use. This loading may be assisted by a loading cartridge or magazine proximate to the jaw mechanism that contains multiple rivets, for example 2 or 3 rivets. These rivets may thus be loaded without egress of catheter assembly 12 from the patient.

The catheter assembly 12 may then be inserted into the patient transfemorally and advanced to the mitral valve, preferably using a transseptal approach. That is, the catheter assembly 12 may be advanced from the femoral vein through the iliac vein, the inferior vena cava, and the right atrium, and across the septum wall into the left atrium, until the distal portion 14 thereof extends between the posterior leaflet 2 and the anterior leaflet 3 of the mitral valve 1. This route requires the least amount of bending or turning and provides the most direct route to the mitral valve leaflets. Minimizing the number of turns may facilitate the rotational control of the distal portion 14 of the catheter assembly 12.

If the distal portion 14 includes echogenic materials, the distal portion may be guided to a position against a leaflet at the coaption line 5 using the assistance of three-dimensional echocaradiography to visualize the distal portion 14 and other components of the device 10.

Figure 5:
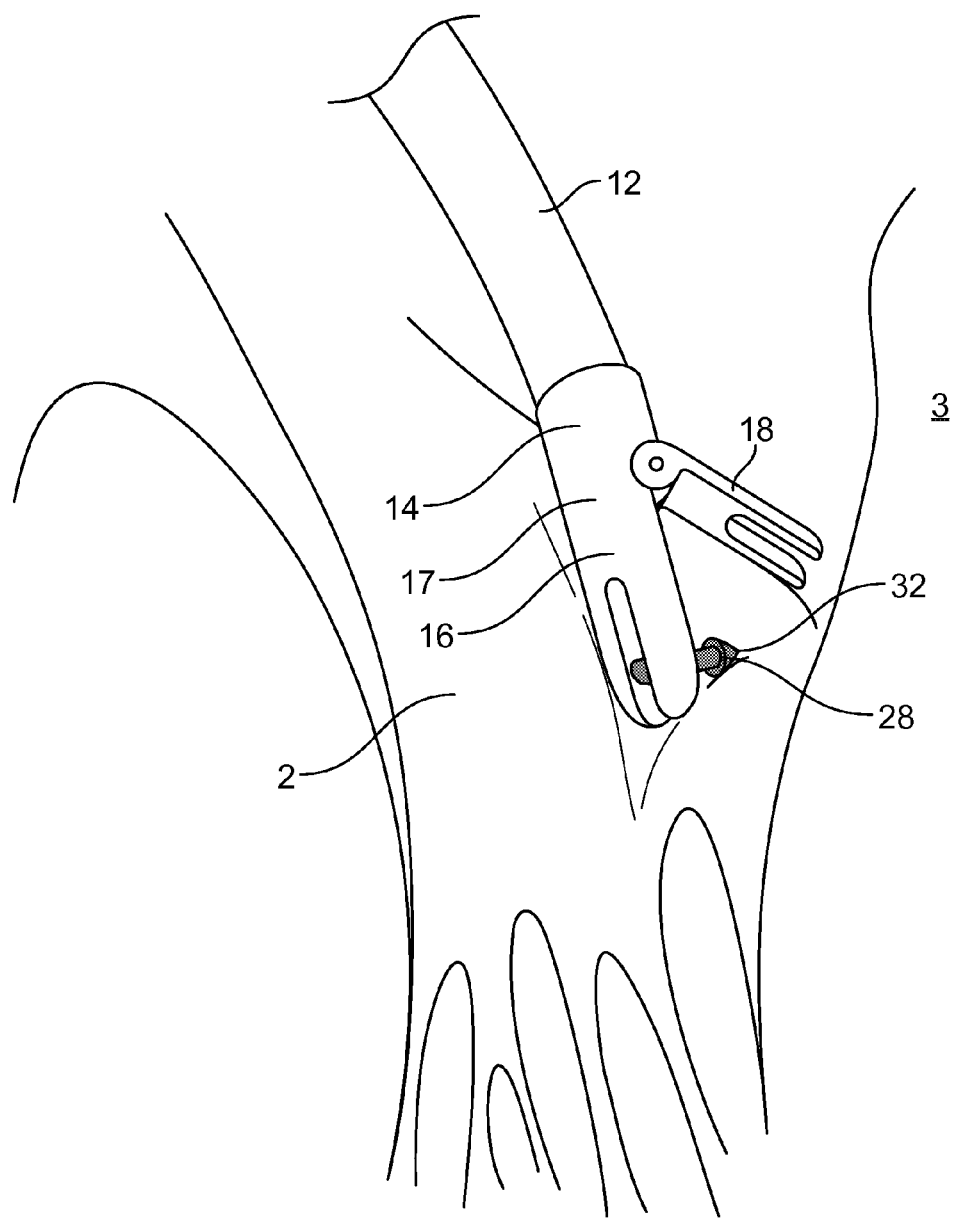
FIGS. 5-8 are illustrations of the sequence of steps for repairing a mitral valve leaflet using the device of FIG. 2.

Turning to FIG. 5, once device 10 has reached the leaflets 2 and 3, jaw 18 may be moved to the open position by operating the actuating member on the device handle. Opening jaw 18 may release the rivet 28 from the stored position within compartment 29 of jaw 16 to the application position.

Figure 6:
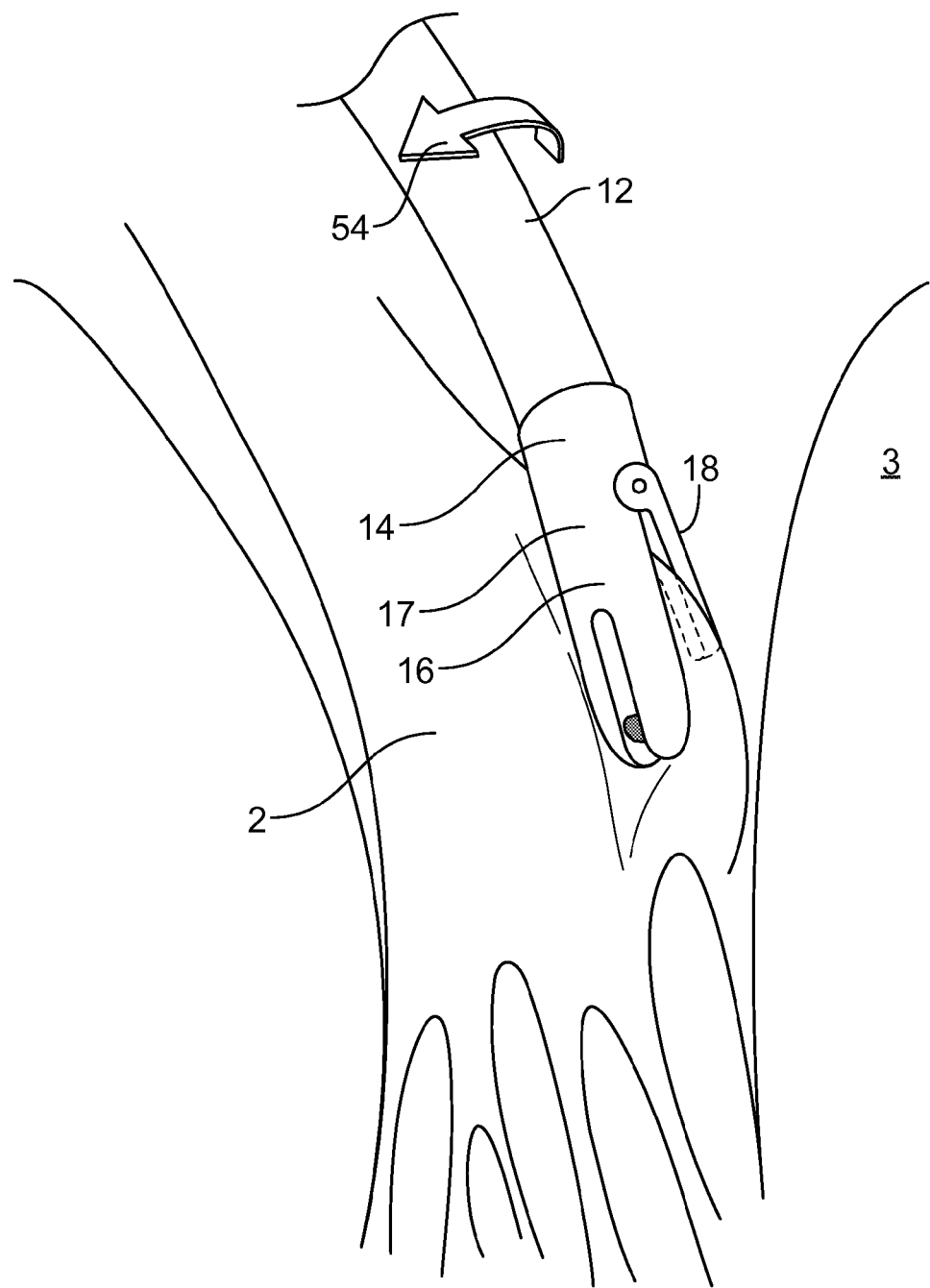

The distal portion 14 of device 10 may then be maneuvered to capture leaflet 2 or 3 (in this example, leaflet 2) in the receiving space between the grasping surfaces 20 and of jaw mechanism 15. Once the leaflet 2 is within the receiving space, jaw 18 may be moved to the closed position, again by operating the actuating member on the device handle. As shown in FIG. 6, moving the jaw 18 toward the closed position may capture the leaflet 2 between jaws 16 and 18. As jaw 18 is closed, it will force the leaflet 2 against the barbed tip 32 of rivet 28, such that the rivet pierces the leaflet at a first location. Continued closing of jaw 18 will cause the barbed tip 32 at the rivet to move through the slot 34 in jaw 18. Once jaw 18 has reached the fully closed position, the leaflet 2 may be held securely in place along the elongated body 30 of rivet 28 and between the gripping surfaces 20 and 22 of jaw mechanism 15.

Figure 7:
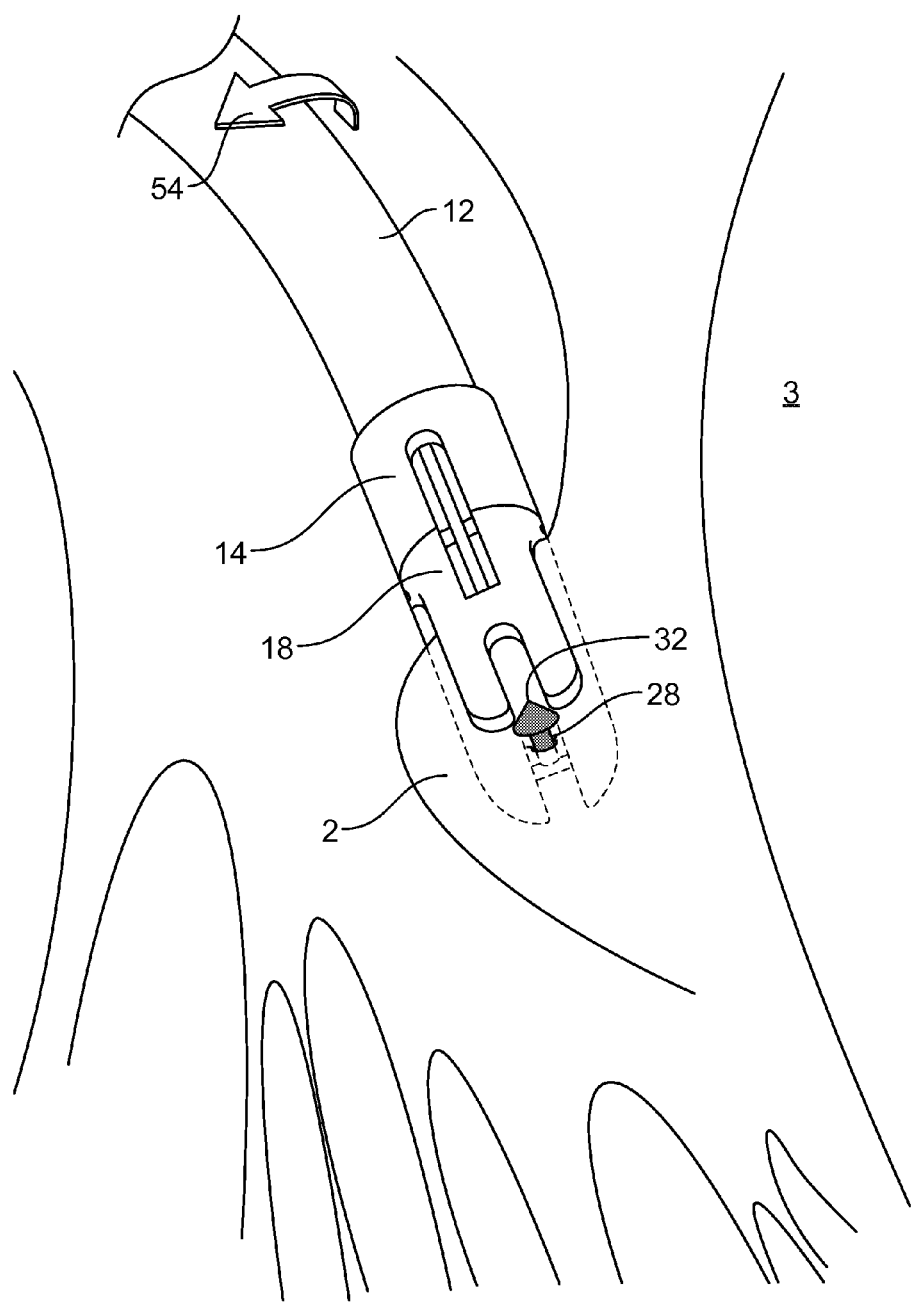

With the leaflet 2 secured within jaw mechanism 15, device 10 may be rotated in a clockwise or counterclockwise direction about the longitudinal axis of the jaw mechanism in order to wrap or fold the leaflet around the other jaw mechanism. Direction arrow 54 indicates the direction of rotation in the examples of FIGS. 6 and 7. Preferably, device 10 is rotated in a direction which causes prongs 25 to engage the tissue of leaflet 2, thereby creating a traction with the leaflet that helps prevent the leaflet from slipping between jaws 16 and 18. FIG. 7 shows device 10 partially rotated, with the barbed tip 32 of rivet 28 having pierced through the leaflet 2.

Figure 8:
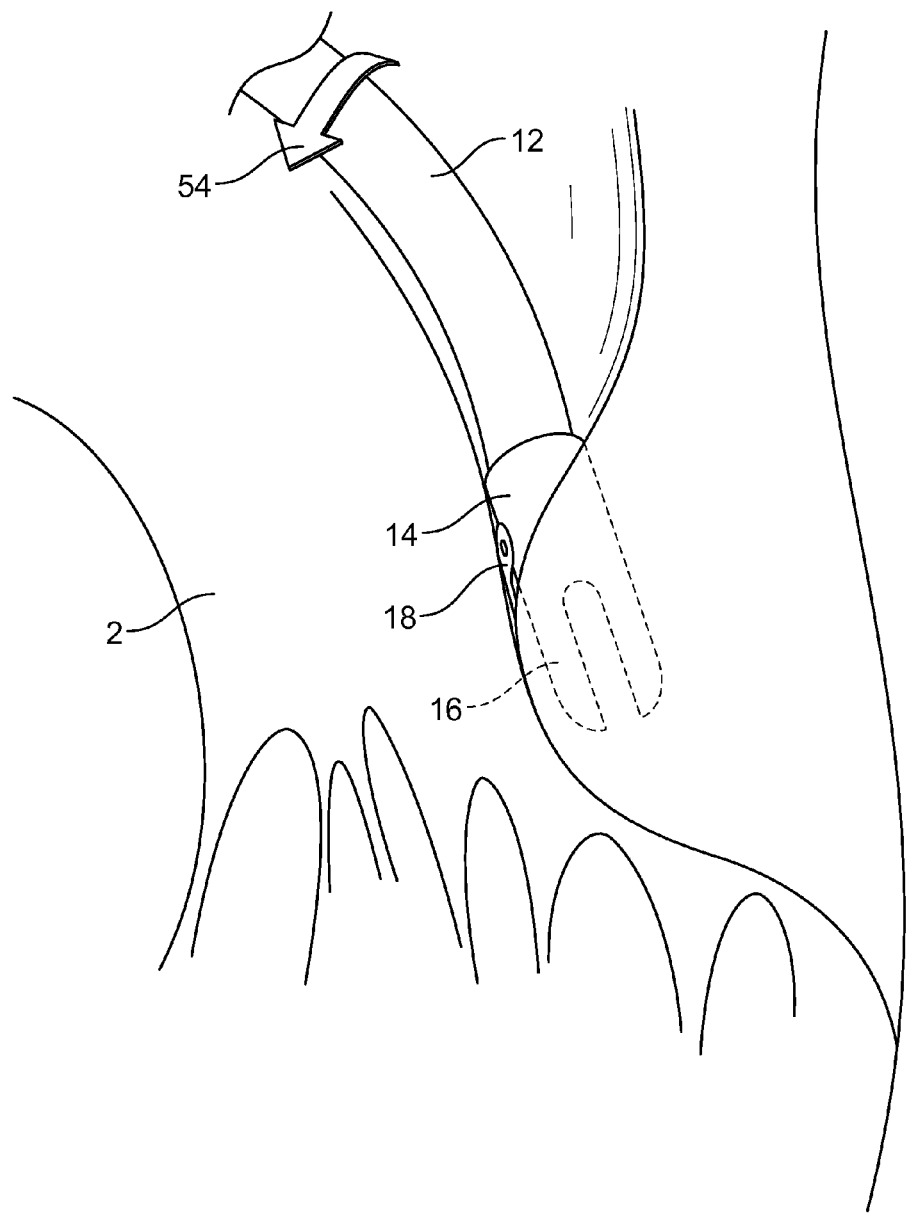

Turning to FIG. 8, once the device 10 has been rotated approximately 180 degrees from the position shown in FIG. 6, the leaflet 2 may be securely wrapped around the outer surface 17 of jaw 16. As device 10 is rotated further, the barbed tip 32 of rivet 28 may again contact and press against the leaflet 2. This pressing and the continued rotation of device 10 may force the barbed tip 32 of rivet 28 to again pierce through leaflet 2 at a second location on the leaflet.

Once rivet 28 has pierced leaflet 2 at the first location and the second location, the rivet may be released from the jaw 16 and will remain in place in the leaflet. Various methods known to those of ordinary skill in the art may be employed to facilitate the release of rivet 28 from jaw 16. For example, the handle of device 10 may include an actuating member for controlling the release of rivet 28. In one arrangement, the actuating member may simply push rivet 28 totally out from compartment 29 in jaw 16. In other arrangement, the actuating member may cause the rupture of a frangible member, either part of rivet 28 or connecting the rivet to jaw 16, thereby releasing the rivet from device 10. For example, a frangible link may be facilitated by a member of stainless steel, of plastic, or of other materials that are more ductile and less brittle designed with an area for stress concentration that will fail in a predictable way. Other examples may include attachment by braided suture, monofilament, or wire by which the connection may be cut and pulled and/or threaded out of the way. In another example, the linkage may be mechanical, whereby the jaw holding the rivet may be moved out of the way or stop applying a force against the rivet when manipulated. The rivet may also be held in place by interference or friction and released by an additional actuating member that applies a force to overcome the friction force. Still further, the actuating member may free rivet 28 from the torsion spring, thereby releasing the rivet. Once rivet 28 has been released from device 10, the device may be removed from the folded leaflet 2 and from the patient.

In one example, the recessed compartment may comprise a slot which may being approximately mid-length of the jaw and extend fully through in the distal direction. The length of the slot may be sufficient to contain rivet 28 when positioned parallel to the surface of the jaw during insertion. Once released, the rivet may position itself perpendicular to the surface of the jaw. The diameter and width of the portion of the base of rivet 28 may be greater than the opening of the slot to avoid passing through the slot. Once deployed and the rivet is disconnected from the delivery system, the slot allows catheter assembly 12 to be removed from within the fold of the tissue by retracting the catheter assembly in the distal direction, allowing the deployed rivet to slide through and out of the slot.

Figure 9:
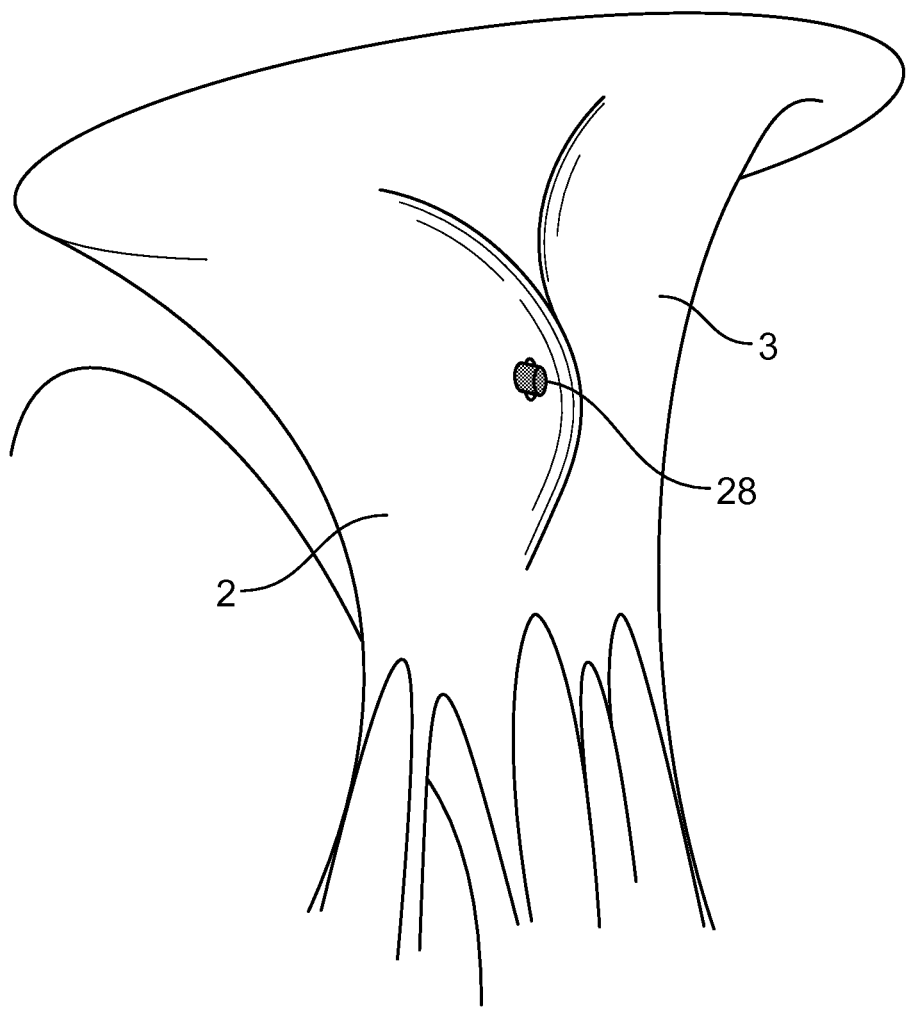
FIG. 9 is an illustration of a repaired mitral valve leaflet.

As shown in FIG. 9, rivet 28 may hold the first and second locations of the leaflet 2 in overlying relationship, creating a fold or pleat in the leaflet. The folding of leaflet 2 may change the shape of the leaflet, tightening loose or floppy tissue therein. This tightening of the leaflet tissue may reduce the likelihood of prolapse and mitral valve regurgitation, thereby repairing the functionality of the valve.

In the devices shown in the figures, particular structures are shown that are adapted to grasp, secure, and repair heart valve leaflet tissue. The invention also contemplates the use of any alternative structures for such purposes, including structures having different lengths, shapes, and configurations.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

INDUSTRIAL APPLICABILITY

The present disclosure can be used to repair heart valve leaflets.

The invention claimed is:

1. A device for repair of a heart valve leaflet, the device comprising:
   an elongated body having a proximal end and a distal end;
   a jaw mechanism on the distal end of the elongated body, the jaw mechanism including a first jaw and a second jaw operable to pivot relative to one another between an open position and a closed position, the jaw mechanism in the open position defining a receiving space between the first jaw and the second jaw, the second jaw including a slot forming a forked edge at a distal end of the second jaw and at least one sharpened structure projecting laterally from the second jaw configure to provide traction for the jaw mechanism when the jaw mechanism is rotated against the tissue of the heart valve leaflet; and
   a rivet mounted to the first jaw and movable from a stored position to an application position, the rivet in the application position projecting away from the first jaw toward the second jaw, the rivet having a sharp free end adapted to pierce the heart valve leaflet,
   wherein movement of the jaw mechanism from the open position to the closed position with the heart valve leaflet in the receiving space and the rivet in the application position causes the rivet to pierce the heart valve leaflet, the slot being sized to receive the sharp free end of the rivet between the forked edge when the rivet is in the application position and the second jaw is in the closed position.

2. The device of claim 1, wherein the first jaw is fixed relative to the elongated body and the second jaw is pivotable relative to the first jaw.

3. The device of claim 2, further comprising an operating mechanism for pivoting the second jaw into the open position.

4. The device of claim 2, further comprising a actuator attached to the jaw at a position distal to a pivot pin, the actuator being configured to pivot the second jaw between the open position and the closed position.

5. The device of claim 1, further comprising a spring element interposed between the rivet and the first jaw for biasing the rivet towards the application position.

6. The device of claim 5, wherein the spring element includes at least one torsion spring.

7. The device of claim 5, wherein the jaw mechanism further includes a includes a structure arranged to cooperate with a tab structure on the rivet in order to limit rotation of the rivet and achieve the application position.

8. The device of claim 1, wherein the first jaw has a compartment for receiving the rivet in the stored position, and the second jaw is configured to overlie at least a portion of the compartment in order to hold the rivet in the compartment when the secured jaw is in the closed position.

9. The device of claim 8, wherein the slot includes an open end between the prongs of the forked edge and an opposite closed end, a length of the slot between the closed end and the open end being less than a length of the compartment measured at a surface of the first jaw, the length of the compartment being greater than the width of the compartment measured at the surface of the first jaw.

10. The device of claim 1, wherein the first jaw has a tissue grasping surface and the second jaw has a tissue grasping surface, the tissue grasping surfaces of the first and second jaws being arranged to confront one another in the closed position, at least one of the tissue grasping surfaces being textured.

11. The device of claim 1, wherein at least a portion of the jaw mechanism is formed from an echogenic material.

12. The device of claim 1, wherein:
the second jaw has a thickness between a first surface facing toward the first jaw and a second surface opposite the first surface; and
the rivet has a length greater than the thickness of the second jaw so that the rivet protrudes beyond the second surface of the second jaw when the second jaw is in the closed position.

13. The device of claim 1, wherein the rivet is configured to be deployed from the first jaw and the slot is sized to allow the deployed rivet to slide through and out of the slot between prongs of the forked edge.

14. The device of claim 1, further comprising a plurality of sharpened structures projecting laterally from an outer edge of the second jaw, the plurality of sharpened structures being configured to provide traction for the jaw mechanism when the jaw mechanism is rotated against the tissue of the heart valve leaflet, the sharpened structure being one of the plurality of sharpened structures.

15. The device of claim 1, wherein the first jaw and the second jaw include complementary curved surfaces arranged to contact one another in the closed position.

16. The device of claim 1, wherein the forked edge includes a pair of pong structures between which the slot is arranged, at least one of the pair of prong structures including the sharpened structure.

17. The device of claim 1, wherein the first jaw includes a second slot forming a second forked edge at a distal end of the first jaw.

18. The device of claim 17, wherein the second forked edge includes a first pair of pong structures between which the second slot is arranged, at least one prong of the first pair of prong structures including a second sharpened structures extending laterally from the first jaw.

19. The device of claim 18, wherein the forked edge includes a second pair of pong structures between which the slot is arranged, at least one prong of the second pair of prong structures including the sharpened structure.

* * * * *